United States Patent
Tsai et al.

(10) Patent No.: US 8,685,262 B2
(45) Date of Patent: Apr. 1, 2014

(54) METHOD FOR MANUFACTURING A NOZZLE PLATE CONTAINING MULTIPLE MICRO-ORIFICES FOR CASCADE IMPACTOR

(71) Applicant: National Chiao Tung University, Hsinchu (TW)

(72) Inventors: Chuen-Jinn Tsai, Hsinchu County (TW); Sheng-Chieh Chen, Taipei County (TW); Hong-Dar Chen, Kaohsiung County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 14/043,239

(22) Filed: Oct. 1, 2013

(65) Prior Publication Data

US 2014/0027406 A1   Jan. 30, 2014

Related U.S. Application Data

(62) Division of application No. 12/805,279, filed on Jul. 22, 2010.

(30) Foreign Application Priority Data

Mar. 1, 2010  (TW) .............................. 99105869 A

(51) Int. Cl.
   *C23F 1/00*   (2006.01)
(52) U.S. Cl.
   USPC ................... 216/37; 216/39; 216/47; 216/56; 216/75; 216/100

(58) Field of Classification Search
   CPC ............ B81C 1/00087; B81C 1/00388; B81C 1/00476; H05K 3/061; G01N 1/2208
   USPC .......................... 216/37, 39, 47, 56, 75, 100
   See application file for complete search history.

(56) References Cited

U.S. PATENT DOCUMENTS

| | | | |
|---|---|---|---|
| 6,431,014 B1 | 8/2002 | Liu et al. | |
| 7,082,811 B2 | 8/2006 | Marple et al. | |
| 7,341,824 B2* | 3/2008 | Sexton | 430/311 |
| 2001/0024219 A1 | 9/2001 | Kanda et al. | |
| 2003/0013046 A1* | 1/2003 | Fonash et al. | 430/314 |

(Continued)

FOREIGN PATENT DOCUMENTS

TW         589253         6/2001

OTHER PUBLICATIONS

Jun-Ho Ji, Gwi-Nam Bae, Jungho Hwang, Observation and Evaluation of Nozzle Clogging in a Micro-orifice Impactor Used for Atmospheric Aerosol Sampling, Particulate Science and Technology, 24: 85-96, 2006.

*Primary Examiner* — Binh X Tran
(74) *Attorney, Agent, or Firm* — Bacon & Thomas, PLLC

(57) ABSTRACT

A nozzle plate containing multiple micro-orifices for the cascade impactor and a method for manufacturing the same are disclosed. The nozzle plate is formed by a series of semiconductor processes, including lithography, etching and electroplating. The nozzle plate comprises a plate body and a plurality of micro-orifices formed on the plate body. The orifice has a diameter which gradually expands in the direction away from the bottom of the plate body to achieve a smooth inner surface, allowing particles to pass therethrough smoothly without being clogged in the nozzle plate.

2 Claims, 2 Drawing Sheets

(56) References Cited

U.S. PATENT DOCUMENTS

2007/0237682 A1* 10/2007 Chuang et al. ............... 422/100
2007/0261240 A1* 11/2007 Sexton et al. ............... 29/890.1
2008/0198202 A1* 8/2008 Shaarawi et al. ............... 347/63
2009/0314742 A1* 12/2009 Kishimoto et al. ............. 216/27
2011/0123932 A1* 5/2011 Guan et al. .................... 430/320

* cited by examiner

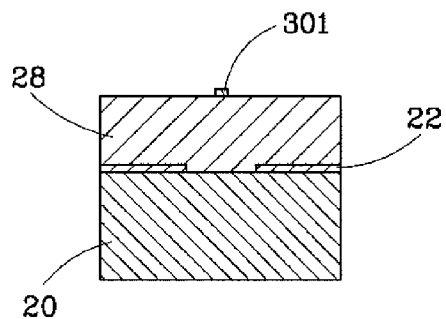
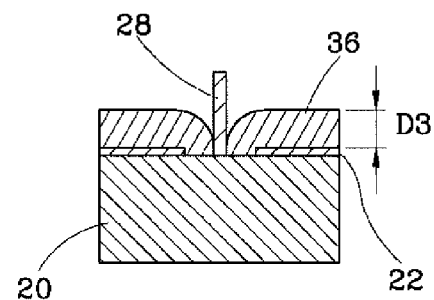
FIG. 7          FIG. 9
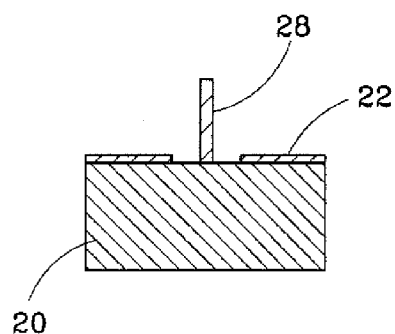
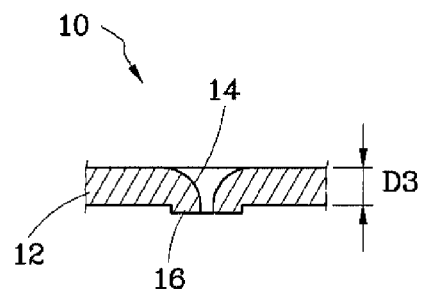
FIG. 8          FIG. 10
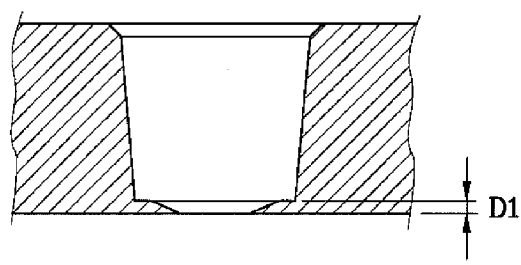
FIG. 11
PRIOR ART

METHOD FOR MANUFACTURING A NOZZLE PLATE CONTAINING MULTIPLE MICRO-ORIFICES FOR CASCADE IMPACTOR

CROSS-REFERENCE TO RELATED APPLICATION

This patent application is a division of U.S. patent application Ser. No. 12/805,279 filed Jul. 22, 2010 entitled "NOZZLE PLATE CONTAINING MULTIPLE MICRO-ORIFICES FOR CASCADE IMPACTOR AND METHOD FOR MANUFACTURING THE SAME", the entire disclosure of which is incorporated herein by reference.

BACKGROUND OF THE INVENTION

1. Field of the Invention

The present invention relates to aerosol sampling technology, and more particularly to a nozzle plate containing multiple micro-orifices for use in a cascade impactor and a method for manufacturing the same.

2. Description of the Related Art

The Micro-Orifice Uniform Deposit Impactor (MOUDI) invented by MSP Corporation has been widely used for size-classified aerosol sampling. Each stage of the MOUDI consists of a nozzle plate with a plurality of nozzles and an impaction plates to collect particles of a specific size range. By decreasing the nozzle diameter and increasing the air jet speed in the nozzle from the top to the bottom stages, the MOUDI is able to collect particles of subsequently smaller size ranges. In a 10 stage MOUDI, the cutoff aerodynamic diameter of the stage 0 to 10 is 18, 10.0, 5.6, 3.2, 1.8, 1.0, 0.56, 0.32, 0.18, 0.1, 0.056 μm, respectively, and there is a final after filter to collect particles smaller than 0.056 μm. To classify very small particles, the nozzle plates of the last 4 impaction stages, or stage 7 to 10, use 900-2000 micro-orifices with the diameter ranging from 140 to 52 μm to collect particles ranging from 0.32 to 0.056 μm in diameter.

U.S. Pat. No. 6,431,014 disclosed an improved MOUDI design with a series of differential pressure sensors for measuring the pressure drop across the nozzle plates. Additionally, the influence of particle accumulation and blockage in the micro-orifices on the performance of the MOUDI is also briefly discussed. The clogged orifices may cause the cut-point of the impactor to change which leads to measurement errors. The dust accumulation problem in the nozzle can be eliminated by periodic cleaning. However, an improper cleaning method, such as high intensity ultrasonic cleaning, may damage the nozzle plates whose wall thickness to define the nozzle diameter is very thin.

Ji et al. (2006) observed the $6^{th}$ to $8^{th}$ stage nozzle plate of a 8-stage MOUDI by using an electron microscope, and the results were published in a journal paper (Ji, J. H., Bae, G. N., Hwang, J., 2006. Observation and evaluation of nozzle clogging in a micro-orifice impactor used for atmospheric aerosol sampling, *Particulate Sci. Technol.* 24: 85-96). In the study, nozzle clogging caused by particle deposition in the nozzle was observed. The collection efficiency curves were shifted to that corresponding to smaller orifice sizes, and the 50% cutoff sizes were much smaller than those specified by the manufacturer for the three stages with nozzles less than 400 μm in diameter. The pressure drops across the clogged nozzles were also higher than the nominal values given by the manufacturer.

The inventor of the present invention used an optical microscope to observe the micro-orifices of the nozzle plate of the last several stages of the MOUDI. An uneven inner surface of the micro-orifices was observed (see FIG. 11). In the current method, the major part of the nozzle is made by the wet etching process while the final bottom part of the orifice has to be made by laser drilling to define a known orifice diameter. Due to the thickness limitation of laser drilling used to manufacture the orifice, the wall thickness D1 at the bottom side of each micro-orifice is only about 10 μm. This is the main reason why there exists an abrupt step at the bottom of the orifice which renders clogging of particles easily. Besides, this fragile structure prevent the nozzle plates from being cleaned effectively, such as by an ultrasonic cleaner. Improvement of the structure and the shape of the micro-orifices for the nozzle plate is therefore critically needed.

SUMMARY OF THE INVENTION

It is the main object of the present invention to provide a nozzle plate with multiple micro-orifices for a cascade impactor and a method for manufacturing the same, wherein the micro-orifices of the nozzle plate have a smooth inner surface, avoiding clogging of particles in the nozzle plate.

It is another object of the present invention to provide a nozzle plate for a cascade impactor and a method for manufacturing the same, wherein the uniform wall thickness and sturdy structure of the micro-orifices facilitate cleaning by an ultrasonic cleaner.

To achieve these and other objects of the present invention, a method for making a nozzle plate containing multiple micro-orifices comprises the steps of:

(1) depositing a seed layer on a substrate; (2) coating the seed layer with a layer of first photoresist, radiating UV light through a first mask onto the first photoresist, and then developing the first photoresist; (3) etching the seed layer and removing the first photoresist, so as to form a plurality of through holes on the seed layer that cut through top and bottom sides of the seed layer; (4) coating a sacrificial layer on the substrate and the seed layer; (5) depositing a metal mask film on the sacrificial layer; (6) coating a layer of second photoresist on the metal mask film, radiating UV light through a second mask onto the second photoresist, and then developing the second photoresist; (7) etching the metal mask film and removing the second photoresist, so as to form a plurality of protrusions on the sacrificial layer; (8) etching the sacrificial layer until the substrate and the seed layer are exposed to the outside; (9) electroplating a metal material onto the seed layer; and (10) removing the substrate, the seed layer and the sacrificial layer. Further, the metal material used during step (9) is a mix of nickel and cobalt.

BRIEF DESCRIPTION OF THE DRAWINGS

FIG. 7 is a schematic drawing showing the fabrication of a nozzle plate containing a plurality of micro-orifices for cascade impactor in accordance with the present invention (VII).

FIG. 8 is a schematic drawing showing the fabrication of a nozzle plate containing a plurality of micro-orifices for cascade impactor in accordance with the present invention (VIII).

FIG. 9 is a schematic drawing showing the fabrication of a nozzle plate containing a plurality of micro-orifices for cascade impactor in accordance with the present invention (IX).

FIG. 10 is a schematic drawing showing the fabrication of a nozzle plate containing a plurality of micro-orifices for cascade impactor in accordance with the present invention (X).

FIG. 11 is a schematic sectional view of a nozzle plate for cascade impactor made according to the prior art design.

DETAILED DESCRIPTION OF THE INVENTION

Figure 1:
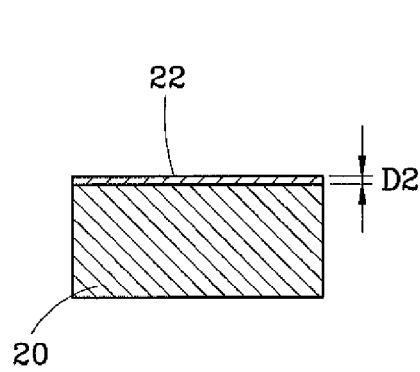
FIG. 1 is a schematic drawing showing the fabrication of a nozzle plate containing a plurality of micro-orifices for cascade impactor in accordance with the present invention (I).
Figure 2:
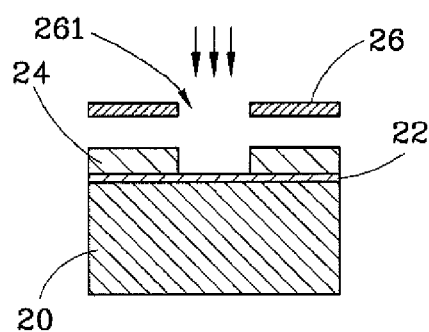
FIG. 2 is a schematic drawing showing the fabrication of a nozzle plate containing a plurality of micro-orifices for cascade impactor in accordance with the present invention (II).
Figure 3:
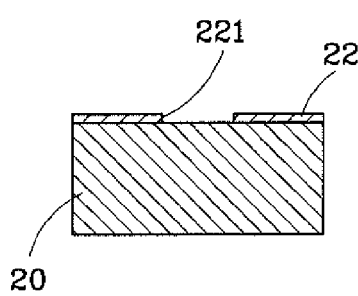
FIG. 3 is a schematic drawing showing the fabrication of a nozzle plate containing a plurality of micro-orifices for cascade impactor in accordance with the present invention (III).
Figure 4:
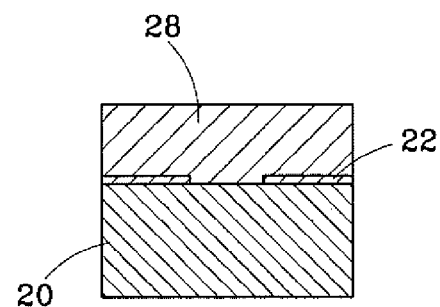
FIG. 4 is a schematic drawing showing the fabrication of a nozzle plate containing a plurality of micro-orifices for cascade impactor in accordance with the present invention (IV).
Figure 5:
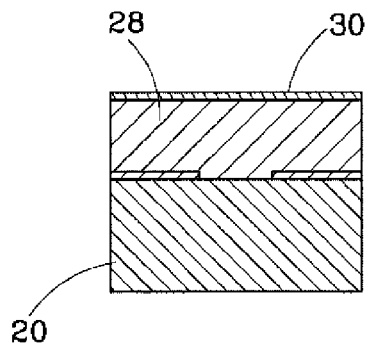
FIG. 5 is a schematic drawing showing the fabrication of a nozzle plate containing a plurality of micro-orifices for cascade impactor in accordance with the present invention (V).
Figure 6:
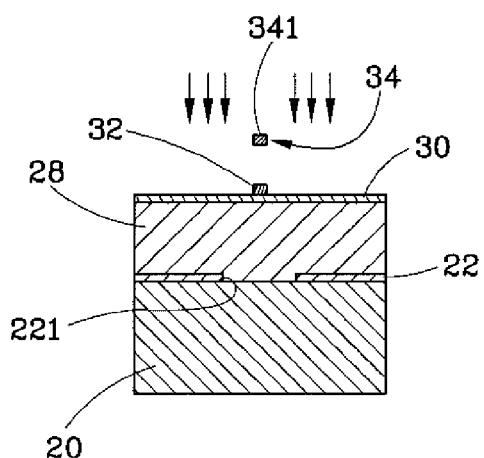
FIG. 6 is a schematic drawing showing the fabrication of a nozzle plate containing a plurality of micro-orifices for cascade impactor in accordance with the present invention (VI).

Referring to FIGS. 1-10, a method for the fabrication of a nozzle plate having multiple micro-orifices for the cascade impactor in accordance with the present invention includes the steps of:

(1) depositing a seed layer 22 on a glass substrate 20, as shown in FIG. 1, wherein copper or chromium can be used to deposit the seed layer 22 by a sputtering process, an evaporation process or a chemical vapor deposition (CVD) process; the seed layer 22 has a thickness D2 about 3 μm;

(2) coating the seed layer 22 with a layer of first photoresist 24, radiating UV light through a first mask 26 onto the first photoresist 24, and then developing the first photoresist 24, as shown in FIG. 2, wherein the first mask 26 has a plurality of transparent regions 261 for the passing of the applied UV light; for the sake of brevity, only one transparent region 261 is seen in FIG. 2;

(3) etching the seed layer 22 and removing the first photoresist 24, as shown in FIG. 3, so as to form a plurality of through holes 221 on the seed layer 22 that cut through top and bottom sides of the seed layer 22;

(4) coating a sacrificial layer 28 on the glass substrate 20 and the seed layer 22, as shown in FIG. 4, wherein the sacrificial layer 28 can be prepared from, for example, but not limited to, polyimide (PI);

(5) using copper or chromium to deposit a metal mask film 30 on the sacrificial layer 28 by a sputtering process, an evaporation process or a chemical vapor deposition process, as shown in FIG. 5;

(6) coating a layer of second photoresist 32 on the metal mask film 30, radiating UV light through a second mask 34 onto the second photoresist 32, and then developing the second photoresist 32, as shown in FIG. 6, wherein the second mask 34 has a plurality of circular opaque regions 341 at locations corresponding to the first through holes 221 on the seed layer 22;

(7) etching the metal mask film 30 and removing the second photoresist 32, as shown in FIG. 7, so as to form a plurality of protrusions 301 on the sacrificial layer 28; for the sake of brevity, only one circular opaque region 341 and one protrusion 301 are respectively seen in FIGS. 6 and 7;

(8) etching the sacrificial layer 28 which is not covered by the protrusions 301 until the glass substrate 20 and the seed layer 22 are exposed to the outside, and the sacrificial layer 28 covered by the protrusions 301 is remained on the substrate 20 as shown in FIG. 8;

(9) electroplating a metal material 36 onto the seed layer 22 to a desired thickness D3, as shown in FIG. 9, wherein the metal material can be, but not limited to, a mix of nickel and cobalt, and the thickness D3 of the metal material 36 is 150 μm; the metal material 36 is also electroplated onto the substrate 20; and

(10) removing the substrate 20, the seed layer 22 and the sacrificial layer 28, thereby obtaining a nozzle plate 10, as shown in FIG. 10, which is to be processed further through a series of cutting and hole-drilling processes for installation in a multi-stage cascade impactor.

Referring to FIG. 10, a nozzle plate 10 for cascade impactor in accordance with the present invention is made through a series of semiconductor processes, including lithography, etching and electroplating. The nozzle plate 10 comprises a plate body 12 and a plurality of micro-orifices 14 cut through top and bottom sides of the plate body 12. Because the nozzle plate 10 is formed by means of electroplating, the micro-orifices 14 have a smooth inner surface and a diameter which expands gradually from the bottom side of the plate body 12 toward the top side thereof. Further, the nozzle plate 10 has an annular protrusion 16 protruded from the bottom side around each of the micro-orifices 14.

Further, the smooth inner surfaces of the micro-orifices 14 allow particles to pass therethrough smoothly without clogging the micro-orifices. Further, the uniform wall thickness and sturdy structure of the micro-orifices 14 facilitate cleaning by an ultrasonic cleaner and improve the convenience of use and the sampling quality. Further, subject to different desired cut-off aerodynamic diameters, the number of the micro-orifices 14 of the nozzle plate 10 and their final orifice diameter can be 900/140 μm, 900/90 μm, 2000/55 μm, 2000/52 μm, 980/49 μm, 1650/450 μm or 2000/55 μm. Preferably, the number of the micro-orifices 14 is within 50-10000, and the diameter is within 45-410 μm.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A method for making a nozzle plate containing multiple micro-orifices, comprising the steps of:

(1) depositing a seed layer on a substrate;

(2) coating the said seed layer with a layer of first photoresist, radiating UV light through a first mask onto said first photoresist, and then developing the first photoresist;

(3) etching said seed layer and removing the said first photoresist, so as to form a plurality of through holes on said seed layer that cut through top and bottom sides of said seed layer;

(4) coating a sacrificial layer on said substrate and said seed layer;

(5) depositing a metal mask film on said sacrificial layer;

(6) coating a layer of second photoresist on the said metal mask film, radiating UV light through a second mask onto the said second photoresist, and then developing the second photoresist;

(7) etching the said metal mask film and removing the said second photoresist, so as to form a plurality protrusions on the said sacrificial layer;

(8) etching the said sacrificial layer which is not covered by the protrusions until said substrate and the said seed layer are exposed to the outside, the sacrificial layer covered by the protrusions being remained on the substrate;

(9) electroplating a metal material onto the said seed layer and the substrate; and

(10) removing the said substrate, the said seed layer and the said sacrificial layer.

2. The method for making a nozzle plate containing multiple micro-orifices as claimed in claim 1, wherein the metal material used during step (9) is a mix of nickel and cobalt.

* * * * *